United States Patent [19]

Nichols

[11] Patent Number: 5,290,570
[45] Date of Patent: Mar. 1, 1994

[54] LOTIONS CONTAINING LIQUID-LOADED POWDER

[75] Inventor: Larry D. Nichols, Arlington, Mass.

[73] Assignee: Purepac, Inc., Elizabeth, N.J.

[21] Appl. No.: 998,633

[22] Filed: Dec. 30, 1992

Related U.S. Application Data

[63] Continuation of Ser. No. 619,728, Nov. 29, 1990, abandoned, which is a continuation-in-part of Ser. No. 358,690, May 30, 1989, Pat. No. 5,000,947.

[51] Int. Cl.$^5$ ............................. A61K 9/14; A61K 7/42
[52] U.S. Cl. ..................................... 424/499; 424/59; 424/405; 514/951
[58] Field of Search ............... 424/489, 494, 69, 499, 424/59, 905; 514/951

[56] References Cited

U.S. PATENT DOCUMENTS

| | | | |
|---|---|---|---|
| 2,891,946 | 6/1959 | Volberg et al. | 260/230 |
| 3,846,404 | 11/1974 | Nichols | 536/76 |
| 3,985,298 | 10/1976 | Nichols | 239/54 |
| 4,024,073 | 5/1977 | Shimigu et al. | 252/316 |
| 4,029,726 | 5/1977 | Nichols | 264/41 |
| 4,046,717 | 9/1977 | Johnston et al. | 252/546 |
| 4,067,824 | 1/1978 | Teng et al. | 252/522 |
| 4,128,507 | 12/1978 | Mitzner | 252/522 |
| 4,193,989 | 3/1980 | Teng et al. | 424/60 |
| 4,369,173 | 1/1983 | Causland et al. | 424/35 |
| 4,383,988 | 5/1983 | Teng et al. | 424/68 |
| 4,597,960 | 7/1986 | Cohen | 424/28 |
| 4,643,856 | 2/1987 | Nichols | 264/41 |
| 4,690,825 | 9/1987 | Won | 424/501 |
| 4,724,240 | 2/1988 | Abrutyn | 514/847 |
| 4,752,496 | 6/1988 | Fellows et al. | 427/27 |
| 4,755,433 | 7/1988 | Patel et al. | 428/422 |
| 4,937,081 | 1/1990 | Kagotani | 424/498 |
| 4,952,402 | 8/1990 | Sparks | 424/419 |
| 5,008,114 | 4/1991 | Lovrecich | 424/484 |

*Primary Examiner*—Thurman K. Page
*Assistant Examiner*—Sally Gardner
*Attorney, Agent, or Firm*—Thomas J. Engellenner

[57] ABSTRACT

An emulsifier-free lotion suspension of at least one liquid in another liquid, the lotion having high intrinsic stability. The lotion is prepared by combining microscopic particles of soft, porous, frangible polymer material containing at least a first liquid with a second liquid in free form. The amount of free liquid is sufficient to achieve a creamy texture without allowing bouyant movement of the particles. The softness of the particles is sufficient to enable the lotion to leave essentially no visible residue when rubbed onto the skin. The polymer material preferably takes the form of a microporous cellulosic powder.

13 Claims, No Drawings

5,290,570

LOTIONS CONTAINING LIQUID-LOADED POWDER

REFERENCE TO RELATED APPLICATION

This application is a continuation of application Ser. No. 07/619,728, filed Nov. 29, 1990 abandoned, which is a continuation-in-part of U.S. Ser. No. 358,690 filed May 30, 1989 (now U.S. Pat. No. 5,000,947, issued Mar. 19, 1991).

BACKGROUND OF THE INVENTION

The present invention relates to emulsifier-free, stabilized lotions.

Lotions are important cosmetic and health formulations, and are common vehicles for delivery of topical skin treatments. Such lotions, which are generally oil-in-water or water-in-oil emulsions, are perceived as convenient, easy to apply and perhaps elegant. They have a pleasant texture, and allow the simultaneous application of water-soluble and oil-soluble ingredients. (Hereinafter the terms "lotion" and "lotions" will be understood generally to encompass personal care cosmetic, health and medical lotions, creams, ointments and the like.)

One consideration in the formulation of lotions containing a mixture of dissimilar liquids is the likelihood of separation of the liquids. Highly emulsified liquids are in a high energy state, i.e., there is a high level of interfacial energy between the molecules of dissimilar liquids. In such mixtures, droplets of like liquid are attracted and are inclined to coalesce and the more bouyant of the mixed liquids is inclined to separate from the other liquid and to rise to the surface of the mixture. Hence, emulsions are inherently unstable and tend to separate, i.e., they tend to seek their low energy state.

In order to achieve adequate shelf-life, cosmetic lotions typically require ingredients, called emulsifiers, to stabilize the emulsion in its otherwise high energy state. Such emulsifiers reduce interfacial energy, making the emulsion less unstable. They may also impede droplet-to-droplet contact and thereby inhibit coalescence.

Emulsifiers serve an essential purpose in a lotion, but are undesirable in topical applications, since they tend to cause skin irritation. Many emulsifying agents are demonstrably irritating: sodium lauryl sulfate, perhaps the most common emulsifier, is employed as a standard irritant in human skin tests. Modern product lotions tend to use less irritating nonionic emulsifiers, but the complete elimination of dermatologically questionable ingredients such as emulsifiers is an increasingly important goal in the formulation of topical lotions.

A generic method for elimination of chemical emulsifiers would be an important step in the campaign against use of irritants. One alternative to the use of chemical emulsifiers might include solidifying the suspended droplets so they cannot merge or circulate. However, any physical method of emulsion stabilization must remain effective over a wide range of liquid surface tensions, densities and viscosities, given the wide range of ingredients compounded into lotions. Furthermore, the end product should be a soft lotion, rather than a gritty slurry, and one which does not leave a visible residue on the skin.

It is therefore an object of the present invention to provide an emulsifier-free stabilized lotion.

It is another object of the present invention to provide an emulsifier-free stabilized lotion which is perceived as a soft emulsion, rather than as a gritty slurry, and does not leave a visible residue on the skin.

SUMMARY OF THE INVENTION

The present invention provides an emulsifier-free lotion suspension of at least one liquid in another liquid, the lotion having high intrinsic stability. The new method of the invention includes the steps of combining microscopic particles of soft, frangible polymer material containing at least a first liquid with a second liquid in free form. The softness of the particles is sufficient to enable the lotion to leave essentially no visible residue when rubbed onto the skin of a human. The amount of free liquid is sufficient to achieve a creamy texture (i.e., smooth and without grit) while minimizing suspension-breaking forces (e.g., bouyant forces due to differences in density, surface tension due to differences in interfacial energy, and, electrostatic forces due to differences in charge, between the particles themselves or between the particles and the surrounding free liquid).

Details of the formation of cellulosic powders can be found in the above-referenced parent application, U.S. Ser. No. 358,690, filed May 30, 1989 (now U.S. Pat. No. 5,000,947), and a commonly-owned, copending application entitled "Process For Producing Liquid-Loaded Powders", by Larry D. Nichols and John F. Cline, U.S. Ser. No. 07/619,236, filed contemporaneously herewith, both of which are incorporated herein by reference. A preferred polymer liquid-loadable powder includes microporous cellulose triacetate prepared by the method of the above application entitled "Process For Producing Liquid-Loaded Powders", U.S. Ser. No. 07/619,736.

In one technique, the liquefiable powders are formed by dissolving a cellulosic polymer and a pore-forming liquid in a volatile, polar solvent (e.g., a low molecular weight halogenated hydrocarbon, ester or diester) and then dispersively evaporating the solution, for example, by spray drying. Suitable volatile solvents for cellulosic polymers include methylene chloride, acetone, ethyl acetate, ethyl carbonate, methyl formate and the like. Methylene chloride is a preferred solvent when the cellulosic polymer is cellulose triacetate. Alternatively, other solvents, such as formic acid or the like, can be used and the resulting solution can be sprayed into a non-solvent such as methanol where the powder particles are then recovered by filtration and rinsing. The active agent can be incorporated into the solvent or introduced by liquid phase substitution after the powder is formed.

The cellulosic powders useful in the present invention can range from about one to about 500 micrometers in average diameter, preferably from about 5 to about 100 micrometers in average diameter, and typically are roughly microspherical in shape. They are further characterized by being microporous with interconnecting pores ranging in size from about one to about 500 nanometers and capable of holding liquid payloads of active agents.

The cellulosic powder can be formed from cellulosic polymers chosen from the group of cellulose acetates, cellulose butyrates, cellulose nitrates, cellulose propionates, ethyl celluloses and discrete or molecular mixtures thereof. One preferred cellulosic powder is a polymeric powder of cellulose triacetate, having a (dry) acetyl content greater than about 42 percent. The liquid content of the cellulosic powders of the present invention can range from about 50 percent to about 95 percent by weight.

A lotion made according to the invention includes a frangible, microporous cellulosic powder having an entrapped liquid A content varying from about 50% to about 95% by weight mixed into a free-form base liquid B. The powder material is sufficiently frangible so as to release the liquid load upon application of frictional force. The particulates are suspended in the base liquid to provide a composition having high intrinsic stability. Liquid B may be water, an alcohol such as propylene glycol, or an emollient oil such as isopropylmyristate, or volatile silicones and cymethicones, for example.

The preferred amount of base liquid B is about 30% to about 60% by volume. However, generally, the amount of base liquid B which is useful for preparing a lotion from a liquid-loaded powder is limited at the lower bound by the need to provide sufficient liquid to completely fill the interstices between the powder particles; failure to do so will produce a stiff, crumbly, putty-like mass. At the upper bound, the amount of liquid should not exceed that at which the powder particles begin to lose contact with each other and become subject to positive or negative bouyant forces; beyond such upper limit, the powder will sink or float and a layer of excess liquid will appear.

Compositions made in accordance with the present invention permit the delivery of effective amounts of prepared ingredients without many of the problems normally associated with liquids, oils, lotions and gels. By assisting in the distribution of delivered agents uniformly over the skin and providing an invisible superficial reservoir to replace active ingredients as they are absorbed into the body or lost to the environment, the compositions of the invention enhance the efficacy, heighten the convenience, and improve the economy of self-administered preparations.

The liquid-loaded, frangible cellulosic powder of the invention, which may be used in the form of a free powder, can be alternatively formulated into a lotion by admixture with a suitable liquid base, but without the use of potentially irritating surfactants or other stabilizers. Yet such lotions are as stable as conventional stabilized emulsions. Liquefiable cellulosic powders are thus suitable for the preparation of stable, minimally irritating, hypoallergenic lotions. Suitable liquid bases for lotion embodiments include water, mineral or silicone oils, volatile silicones, and moisturizing agents such as glycerin or propylene glycol.

In practice of the above invention, the microscopic frangible particles of soft polymer material may be loaded with an emollient oil, a perfume, a coloring agent, or a dermatologically beneficial liquid, such as a sun screen, an analgesic (e.g., for relief of skin or muscle discomfort), an insect repellent, or foot care compound (e.g., an antifungal), for example. The dermatologically beneficial liquid may also include an emollient oil, perfume or coloring agent.

It is a feature of the present invention that smooth, even unexpectedly smooth, lotion compositions can be manufactured which have a long, even a prolonged, shelf-life. Hence incompatible liquids (e.g., oil and water) have a reduced tendency of separation in practice of the presently disclosed lotion formulation. Furthermore, the liquids held within the polymer material may experience a lower degree of oxidation or rate of evaporation compared to the same liquids in lotions not having the liquid loaded polymers of the present invention.

The invention will next be described in connection with certain exemplary methods and compositions. However, it should be clear that various additions, subtractions and changes can be made by those skilled in the art without departing from the spirit or scope of the invention.

DETAILED DESCRIPTION OF THE PREFERRED EMBODIMENT

The present invention provides a stable, emulsifier-free lotion suspension of at least one liquid in another liquid. The lotion suspension technique may be understood as a droplet solidification process which mitigates the separation tendency of dissimilar liquids in the lotion but without introduction of perceptible grit or residue.

In accordance with an embodiment of the invention, an emulsifier-free A-in-B emulsion is prepared by incorporating liquid A into microscopic Particles of a soft, high-liquid-content, frangible, polymeric powder such as described above. This liquid-containing Powder is then blended with enough liquid B to achieve a smooth lotion without allowing bouyant motion of individual particles.

Lotions made according to the invention leave no perceptible residue on the skin because the small amount of polymer needed to stabilize liquid A in particulate form is too weak and frangible to survive mild abrasion. When rubbed, the polymer releases its liquid payload and apparently disappears. The polymer is still invisibly present on the skin, but unlike surfactants, most polymers show no skin irritancy. Surprisingly, there are no surfactants, emulsifiers, or other additives required to achieve a uniform and stable lotion even when water and a highly hydrophobic oil are employed as the two liquids.

EXAMPLES

The examples below illustrate preparation of lotions according to the invention.

EXAMPLE A: Emollient-Loaded Lotion

The spray evaporative method referred to above was used to prepare a white powder having 15% cellulose triacetate and 85% octyldodecanol, a common emollient oil. Microscopic examination revealed spherical particles with diameters lying primarily between 25 and 100 microns. 2.5 Grams of water was added to 2.0 grams of this powder with gentle swirling, producing a smooth white lotion which did not flow under its own weight. When the lotion was transferred by fingertip to the skin of the palm or wrist, the lotion was easy to spread and apparently disappeared completely upon mild rubbing. A pleasant cooling sensation was produced as the water evaporated, and the desired emollient action of the oil could be felt on the skin.

EXAMPLE B: Sunscreen-Loaded Lotion

Suncreens can be usefully incorporated into a lotion of the invention for better topical action of the sunscreen. For example, sunscreen materials such as amyl-p-dimethylaminobenzoate, oxybenzone, homomethyl salicylate, mono-p-aminobenzoate, or 2-ethoxyethyl-p-methoxycinnanate can be incorporated in cellulosic powders by the techniques described above. Such sunscreens can be formulated as solutions in oils and fatty esters such as isopropyl myristate, as well as ethanol, isopropyl alcohol or other alcohols. These liquid solutions can be loaded as liquid A into the polymer powder in the spray drying manner described above. The liquid-loaded powder is then mixed with a base liquid B, e.g., 30-60% water, to produce a lotion according to the invention.

EXAMPLE C: Analgesic-Loaded Lotion

Analgesics can be usefully incorporated into a lotion of the invention for better topical delivery thereof. For example, analgesics or counter-irritants such as menthol, eucalyptol, camphor and methyl salicylate, as well as anti-inflammatories such as cortisone and non-steroidal anti-inflammatories such as triethanolamine salicylate can be incorporated into cellulosic powders as described above. Such analgesics can be formulated as solutions in oils and heavy esters as well as in ethanol, isopropyl alcohol or other alcohols and glycols. These liquid solutions can be loaded as liquid A into the polymer powder in the spray drying manner described above. The liquid-loaded powder is then mixed with a base liquid B, e.g., 30-60% water, to produce a lotion according to the invention.

EXAMPLE D: Insect Repellent-Loaded Lotion

Insect repellents can be usefully incorporated into a lotion of the invention for better topical delivery thereof. For example, insect repellents such as diethyltoluamide and 2-ethyl-1,3-hexamediol can be incorporated into cellulosic powders as described above. Such insect repellents can be formulated as solutions in light or heavy esters as well as in ethanol, isopropyl alcohol or other alcohols or glycols. These liquid solutions can be loaded as liquid A into the polymer powder in the spray drying manner described above. The liquid powder is then mixed with a base liquid B, e.g., 30-60% water, to produce a lotion according to the invention.

EXAMPLE E: Foot Care Agent-Loaded Lotion

Foot care products can be usefully incorporated into a lotion of the invention for better topical delivery thereof. For example, foot care products or fungicides, such as tolnaftate and the like as well as antiseptics, such as phenol, antiperspirants such as aluminum chlorhydrate, and/or deodorant fragrances can be incorporated into cellulosic powders as described above. Such products can be formulated as solutions in emollient oils and esters as well as in ethanol, isopropyl alcohol or other alcohols. These liquid solutions can be loaded as liquid A into the polymer powder in the spray drying manner described above. The liquid-loaded powder is then mixed with a base liquid B, e.g., 30-60% water, to produce a lotion according to the invention.

EXAMPLE F: Perfume-Loaded Lotion

Perfumes can be usefully incorporated into a lotion of the invention for better topical delivery thereof. Such perfumes may include such materials of common practice as esters, alcohols, ketones, and aldehydes, linear, branched or cyclic, saturated or unsaturated, of low, intermediate or high molecular weight. The active ingredients employed may individually posses pleasant odors, or they may have odors which would be undesirable alone but which pleasantly modify other odors, or they may improve the persistence or rendition of other fragrant ingredients. Such perfumes can be formulated as solutions in oils and emollient esters as well as in ethanol, isopropyl alcohol or other alcohols. These liquid solutions can be loaded as liquid A into the polymer powder in the spray drying manner described above. The liquid-loaded powder is then mixed with a base liquid B, e.g., 30-60% water, to produce a lotion according to the invention.

Alternative embodiments of the invention may include a lotion having a nominal color and the loaded liquid having a different color which dominates the lotion only after the lotion is applied to the skin at which time the loaded liquid is released by rubbing action. Furthermore, a plurality of liquid-loaded powders may be mixed together in the same lotion combination, where the liquid contents of the loaded powders then combine their effects only upon application of the lotion and rubbing. Various combinations of liquids may be delivered in this manner for a variety of beneficial effects. For example, two loaded liquids may be mixed in one lotion where the lotion color, aroma, etc., before rubbing essentially is dominated by the base liquid and the Powder material, and the character of the lotion after rubbing is dominated by the released and reacted loaded liquids.

It will thus be understood that, regardless of the embodiment, various additives can be mixed together with the liquid-loaded powder particles (or liquid base) including, for example, talc, cornstarch, waxes, silicones, analgesics, cosmetics, fragrances, lubricants, emollients, moisturizers, medications and other personal care agents, and colorants, pearlescent agents, and mixtures of such additives. It will be understood therefore that the above description describes only several embodiments of the present invention, and that other embodiments are within the spirit and scope of the present invention. Hence, the above description is provided by way of illustration and not by way of limitation. The invention is further defined as set forth in the claims.

What is claimed is:

1. An emollient lotion composition comprising a liquid-containing microporous cellulosic powder material having an entrapped liquid agent content varying from about 50% to about 95% by weight, the cellulosic powder material formed by spray evaporation of a solution of a cellulosic polymer and a pore-forming solvent as powder particles having an average diameter varying from about one to 500 microns, said particles being frangible and being further characterized as microporous with interconnecting pores ranging in size from about one to about 500 nanometers, said liquid agent being loaded within said pores, said particles being sufficiently frangible so as to release the liquid agent upon application of frictional force, and a base liquid for the powder material, wherein the particles are suspended in the base liquid to provide a stable, emollient lotion composition and the base liquid constitutes about 30 percent to about 60 percent of the composition by volume.

2. The composition of claim 1 wherein the powder particles are comprised of microporous cellulose triacetate.

3. The composition of claim 1 wherein the powder particles are between 15 and 150 microns in diameter.

4. The composition of claim 1 wherein the powder particles are between about 25 and about 100 microns in diameter.

5. The composition of claim 1 wherein the cellulosic powder material is selected from the group consisting of cellulose nitrates, cellulose acetates, cellulose propionates, cellulose butyrates and mixtures thereof, formed as porous particulates.

6. The composition of claim 1 wherein the liquid agent includes a dermatologically beneficial material.

7. The composition of claim 6 wherein the liquid agent comprises an active ingredient chosen from the group consisting of emollients, perfumes, sunscreens, insect repellents, topical analgesics, coloring agents and foot care compounds.

8. The composition of claim 1 wherein the entrapped liquid agent comprises an emollient.

9. The composition of claim 1 wherein the entrapped liquid agent comprises a sunscreen agent.

10. The composition of claim 1 wherein the entrapped liquid agent comprises a topical analgesic.

11. The composition of claim 1 wherein the entrapped liquid agent comprises a perfume agent.

12. The composition of claim 1 wherein the entrapped liquid agent comprises a foot care agent.

13. The composition of claim 1 wherein the entrapped liquid agent comprises an insect repellent.

* * * * *